United States Patent
Miura et al.

(10) Patent No.: US 8,337,554 B2
(45) Date of Patent: Dec. 25, 2012

(54) SKIN SUBSTITUTE MEMBRANE, MOLD, AND METHOD OF EVALUATING EXTERNAL PREPARATION FOR SKIN

(75) Inventors: Yoshimasa Miura, Kanagawa (JP); Hiroko Mizuno, Kanagawa (JP); Masato Hatao, Kanagawa (JP); Motoki Ooguri, Kanagawa (JP); Yusuke Hara, Kanagawa (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 13/347,203

(22) Filed: Jan. 10, 2012

(65) Prior Publication Data

US 2012/0109300 A1     May 3, 2012

Related U.S. Application Data

(63) Continuation of application No. 12/996,859, filed on Dec. 8, 2010, now abandoned.

(30) Foreign Application Priority Data

Jun. 13, 2008     (JP) .................................. 2008-155936

(51) Int. Cl.
  *A61F 2/10*   (2006.01)
  *B22C 9/22*   (2006.01)
  *A61B 5/00*   (2006.01)

(52) U.S. Cl. .................... 623/15.12; 249/55; 600/36

(58) Field of Classification Search .................. None
See application file for complete search history.

(56) References Cited

U.S. PATENT DOCUMENTS

| | | | |
|---|---|---|---|
| 5,500,533 | A | 3/1996 | Ogawa et al. |
| 7,004,969 | B2 | 2/2006 | Ishikubo et al. |
| 2002/0045941 | A1 | 4/2002 | Ishikubo et al. |
| 2003/0109927 | A1* | 6/2003 | Ishikubo et al. ........... 623/15.12 |
| 2010/0012850 | A1 | 1/2010 | Miura et al. |
| 2010/0014069 | A1 | 1/2010 | Miura et al. |

FOREIGN PATENT DOCUMENTS

| | | |
|---|---|---|
| JP | 2002-048789 | 2/2002 |
| JP | 3337832 | 10/2002 |
| JP | 2008-096151 | 4/2008 |
| JP | 2008-111834 | 5/2008 |

OTHER PUBLICATIONS

Ferrero et al ("Importance of Substrate Roughness for In Vitro Sun Protection Assessment," IFSCC Magazine, 2006+06, vol. 9, No. 2, p. 97-p. 108).*
Akira Ishikubo, et al., "Shinki In Vitro Shigaisen Bogyosei Hyokaho no Kaihatsu", Journal of SCCJ, Mar. 20, 2003, vol. 37, No. 1, pp. 10 to 16.
Colipa Guidelines, Method for the In Vitro Determination of UVA Protection Provided by Sunscreen Products, Edition of 2007, 2007, p. 2-p. 20.
Ferrero L. et al., Importance of Substrate Roughness for In vitro Sun Protection Assessment, IFSCC Magazine, Jun. 2006, vol. 9, No. 2, p. 97-p. 108.
International Sun Protection Factor Test Method, (COLIPA, JCIA, CTFA SA, CTFA), May 2006.
CIE Research Note, vol. 6, No. 1, 1987.
Miura, Y. et al.; "Photochemistry and Photobiology," 2008, 84, 1569-1575.
Stanfield J: "Optimizing in vitro measurement of sunscreen protection", SOFW-Journal Seifen, Oele, Fette, Wachse, Verlag Fur Chemische Industrie, Augsburg, DE, vol. 132, No. 7, Jul. 1, 2006, pp. 19-23, XP008129662.
Reece B T et al: "An In Vitro Method for Screening Sunscreen Formulations for Sunprotection Factor Using a Full-Thickness Skin Model" Journal of the Society Cosmetic Chemists, US, vol. 43, Nov. 1, 1992, pp. 307-312, XP001117730.
International Search Report mailed Jun. 16, 2009.
Extended European Search Report mailed Jul. 13, 2011.
IPRP mailed Jan. 11, 2011.

* cited by examiner

*Primary Examiner* — Suzanne Ziska
(74) *Attorney, Agent, or Firm* — IPUSA, PLLC

(57) ABSTRACT

A skin substitute membrane includes a surface on one side including a groove-shaped depressed portion and a planar portion, the depressed portion having a cross section having a chamfered V-letter shape, the surface having an arithmetic mean roughness Sa of more than or equal to 10 μm to less than or equal to 50 μm. The depressed portion has a width of more than or equal to 50 μm to less than or equal to 500 μm and a depth of more than or equal to 30 μm to less than or equal to 150 μm. A spectral transmittance for light of more than or equal to 290 nm to less than or equal to 400 nm in wavelength is more than or equal to 50% and less than or equal to 100%.

14 Claims, 8 Drawing Sheets

SKIN SUBSTITUTE MEMBRANE, MOLD, AND METHOD OF EVALUATING EXTERNAL PREPARATION FOR SKIN

CROSS-REFERENCE TO RELATED APPLICATIONS

This application is a continuation of and claims the benefit of priority from U.S. Ser. No. 12/996,859, filed Dec. 8, 2010, now abandoned which claims the benefit of priority from Japanese Patent Application No. 2008-155936, filed Jun. 13, 2008, the entire contents of each of which are incorporated herein by reference.

TECHNICAL FIELD

The present invention relates to a skin substitute membrane, a mold, and a method of evaluating an external preparation for skin.

BACKGROUND ART

Conventionally, the in vivo SPF is used as a scale representing the ultraviolet radiation protection effect of external preparations for skin for preventing sunburn due to ultraviolet radiation, such as sun protection products. This SPF, which is an index indicating the effect of skin protection from sunburn due to ultraviolet radiation and sunburn prevention, is defined by the value obtained by dividing the amount of ultraviolet radiation necessary for causing slight redness in the case of using an external preparation for skin by the amount of ultraviolet radiation necessary for causing slight redness in the case of not using an external preparation for skin. For example, sunburn is ten times less likely to be caused with use of a sun protection product of in vivo SPF 10 than in the case of bare skin.

The in vivo SPF may be measured by exposing each of skin protected by an external preparation for skin and unprotected skin to a certain amount of ultraviolet radiation and determining the next day whether sunburn (erythema) has been caused using artificial light very close to sunlight (a solar simulator).

Use of the in vivo SPF makes it possible to objectively evaluate the ultraviolet radiation protection effect of external preparations for skin. However, measuring the in vivo SPF necessitates the cooperation of a large number of volunteers of specific skin types, thus requiring a large amount of money and a large number of days.

Therefore, Patent Documents 1 through 3 disclose in vitro SPF evaluation methods that measure estimated in vitro SPFs without using volunteers. Further, a polyethylene sheet, a nylon film (see Patent Document 4), a quartz plate, a PMMA plate (see Non-Patent Documents 1 and 2), etc., are known as skin substitute membranes used for in vivo SPF evaluation methods. On a surface of one side of the nylon film of Patent Document 4, grooves with V-shaped vertical sections in a shorter-side direction, imitating sulci cutes, are provided, and irregularities are provided in the part other than the sulci cutes by blasting.

On the other hand, Non-Patent Document 3 determines that the amount of an external preparation for skin applied in measuring in vivo SPFs should be 2.00 mg/cm$^2$. However, no known skin substitute membrane allows an external preparation for skin to be evenly applied with such an amount of application. In the case of using a known skin substitute membrane, the amount of application of the skin substitute membrane in measuring estimated in vitro SPFs is approximately 0.75 mg/cm$^2$ to approximately 1.20 mg/cm$^2$.

Further, when a material subject to degradation due to ultraviolet radiation is used as an ultraviolet absorber contained in an external preparation for skin, the degradation of the ultraviolet absorber progresses at the time of measuring in vivo SPFs. There is doubt as to whether conditions for measuring in vivo SPFs are sufficiently reproduced in the estimated in vitro SPFs of an external preparation for skin containing such a ultraviolet absorber because the amount of application of the external preparation for skin is different from that in the case of measuring in vivo SPFs. Here, causing the amount of application of the external preparation for skin in measuring estimated in vitro SPFs to be 2.00 mg/cm$^2$, which is the same as in the case of measuring in vivo SPFs, is important in reproducing a condition for measuring in vivo SPFs for not only an attenuation pattern in the case of degradation caused by ultraviolet radiation but also the condition of application of the external preparation for skin at a microscopic level.

[Patent Document 1] Japanese Patent No. 3337832
[Patent Document 2] Japanese Laid-Open Patent Application No. 2008-96151
[Patent Document 3] Japanese Laid-Open Patent Application No. 2008-111834
[Patent Document 4] Japanese Laid-Open Patent Application No. 2002-48789
[Non-Patent Document 1] Ferrero, L. et al.; "Importance of Substrate Roughness for In Vitro Sun Protection Assessment," IFSCC Magazine, Vol. 9, No. 2, 97-108 (2006)
[Non-Patent Document 2] COLIPA GUIDELINES, METHOD FOR THE IN VITRO DETERMINATION OF UVA PROTECTION PROVIDED BY SUNSCREEN PRODUCTS, Edition of 2007
[Non-Patent Document 3] International Sun Protection Factor Test Method, (COLIPA, JCIA, CTFA SA, CTFA), May 2006

DISCLOSURE OF THE INVENTION

Problems to be Solved by the Invention

In view of problems of the above-described conventional art, the present invention has an object of providing a skin substitute membrane that makes it possible to measure the ultraviolet radiation transmission characteristic and/or reflection characteristic of an external preparation for skin with accuracy, a mold used for manufacturing the skin substitute membrane, and a method of evaluating an external preparation for skin using the skin substitute membrane.

Means for Solving the Problems

According to an aspect of the invention, a skin substitute membrane includes a surface on one side including a groove-shaped depressed portion and a planar portion, the depressed portion having a cross section having a chamfered V-letter shape, the surface having an arithmetic mean roughness Sa of more than or equal to 10 μm to less than or equal to 50 μm, wherein the depressed portion has a width of more than or equal to 50 μm to less than or equal to 500 μm and a depth of more than or equal to 30 μm to less than or equal to 150 μm, the skin substitute membrane has a thickness of 0.2 mm to 5 mm, and a spectral transmittance for light of more than or equal to 290 nm to less than or equal to 400 nm in wavelength is more than or equal to 50% and less than or equal to 100%, and the planar portion is provided with chamfered roughness, and has an arithmetic mean roughness Sa of more than or equal to 0.1 μm to less than or equal to 30 μm.

According to an aspect of the invention, a skin substitute membrane includes a surface provided with chamfered roughness and having an arithmetic mean roughness Sa of more than or equal to 13 μm to less than or equal to 30 μm, wherein the skin substitute membrane has a thickness of 0.2 mm to 5 mm, and a spectral transmittance for light of more than or equal to 290 nm to less than or equal to 400 nm in wavelength is more than or equal to 50% and less than or equal to 100%.

According to an aspect of the invention, a mold includes a surface on one side including a recess, the recess having a projecting portion and a planar portion formed at a bottom surface of the recess, the bottom surface of the recess having an arithmetic mean roughness Sa of more than or equal to 10 μm to less than or equal to 50 μm, the projecting portion having a cross section having a chamfered inverse V-letter shape, wherein the projecting portion has a width of more than or equal to 50 μm to less than or equal to 500 μm and a height of more than or equal to 30 μm to less than or equal to 150 μm, and the planar portion is provided with chamfered roughness, and has an arithmetic mean roughness Sa of more than or equal to 0.1 μm to less than or equal to 30 μm.

According to an aspect of the invention, a method of evaluating an external preparation for skin includes the steps of applying the external preparation for skin on either skin substitute membrane as set forth above; and measuring an ultraviolet radiation transmission characteristic and/or reflection characteristic of the external preparation for skin by exposing the skin substitute membrane having the external preparation for skin applied thereon to light containing ultraviolet radiation.

According to an aspect of the invention, a mold includes a surface on one side including a recess, the recess being provided with chamfered roughness and having an arithmetic mean roughness Sa of more than or equal to 13 μm to less than or equal to 30 μm.

Effects of the Invention

According to the present invention, it is possible to provide a skin substitute membrane that makes it possible to measure the ultraviolet radiation transmission characteristic and/or reflection characteristic of an external preparation for skin with accuracy, a mold used for manufacturing the skin substitute membrane, and a method of evaluating an external preparation for skin using the skin substitute membrane.

Figure 1:
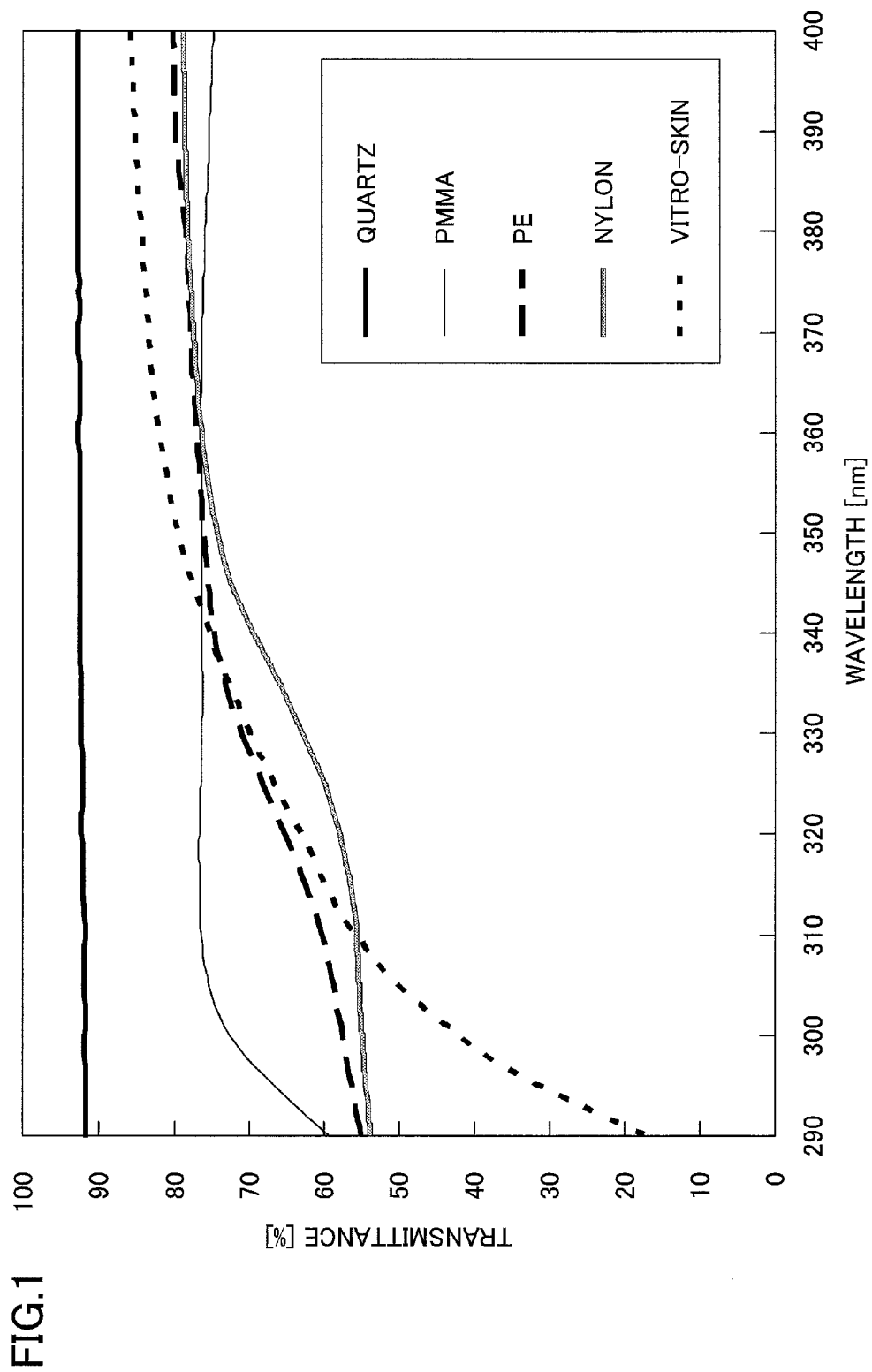
FIG. 1 is a graph illustrating spectral transmittances for light of 290 nm to 400 nm in wavelength.

DESCRIPTION OF THE REFERENCE NUMERALS 1 skin substitute membrane
2 depressed portion
3 planar portion
1' recess
2' projecting portion
3' planar portion
10 mold

BEST MODE FOR CARRYING OUT THE INVENTION

Next, a description is given with the drawings of best modes for carrying out the present invention.

First Embodiment

A skin substitute membrane of this embodiment has a surface with an arithmetic mean roughness Sa of 13 μm to 30 μm, preferably 15 μm to 25 μm. Further, the skin substitute membrane of this embodiment has a spectral transmittance of 50% to 100%, more preferably 60% to 100%, for light of 290 nm to 400 nm in wavelength. As a result, a skin substitute membrane is obtained that makes it possible to measure the ultraviolet radiation transmission characteristic and/or reflection characteristic of an external preparation for skin with accuracy. Such a skin substitute membrane allows reproduction of the amount of application of an external preparation for skin in measuring in vivo SPFs determined in Non-Patent Document 3, which is 2.00 mg/cm$^2$, and is therefore particularly effective in evaluating the estimated in vitro SPFs of an external preparation for skin subject to degradation due to ultraviolet radiation.

At this point, if the arithmetic mean roughness Sa of the surface of the skin substitute membrane is less than 13 μm, it becomes difficult to cause the amount of application in evaluating the external preparation for skin to be 2.00 mg/cm$^2$. On the other hand, if the arithmetic mean roughness Sa of the surface of the skin substitute membrane exceeds 30 μm, the difference from the arithmetic mean roughness Sa of the surface of skin increases. Therefore, even if the amount of application in evaluating the external preparation for skin is caused to be 2.00 mg/cm$^2$, it is difficult to reproduce conditions in evaluating the external preparation for skin in vivo, such as the condition of application of the external preparation for skin at a microscopic level and an attenuation pattern in the case of degradation due to ultraviolet radiation.

Further, if the spectral transmittance of the skin substitute film for light of 290 nm to 400 nm in wavelength is less than 50%, the accuracy of the ultraviolet radiation transmission characteristic and/or reflection characteristic of the external preparation for skin is insufficient.

According to the skin substitute membrane of this embodiment, usually, the arithmetic mean roughness Sa of the surface of one side is 13 µm to 30 µm, but the arithmetic mean roughness Sa of the surfaces of both sides also may be 13 µm to 30 µm.

The arithmetic mean roughness Sa, which is an extension of a two-dimensional arithmetic mean roughness Ra to a three dimension, is the quotient of the volume of the part surrounded by a surface-shape curved surface and an average plane divided by a measured area. Letting the average plane be an xy plane, the vertical directions be the z-axis, and the measured surface shape curved line be z=f(x, y), the arithmetic mean roughness Sa is defined by:

$$Sa = \frac{1}{LxLy}\int_0^{Lx}\int_0^{Ly} f(x, y)dxdy.$$

(In the equation, Lx is a measured length in an x direction, and Ly is a measured length in a y direction.)

A description is given below of the reason why it is preferable to use the arithmetic mean roughness Sa in place of the JIS-defined surface roughness Ra in order to define the surface of the skin substitute membrane of this embodiment. Like the surface of skin, the surface of the skin substitute membrane of this embodiment is dotted with depressed portions. Therefore, it is necessary to determine the shape of the surface of the skin substitute membrane with a representative value of surface roughness that does not depend on the point of measurement.

Such a surface includes parts where there are depressed portions and parts where there are no depressed portions. Therefore, the surface roughness Ra may differ greatly depending on the point of measurement. Accordingly, the surface roughness Ra may vary greatly from measurement to measurement depending on the microscopic shape of the surface, thus making it difficult to define the shape of the surface.

On the other hand, the arithmetic mean roughness Sa is determined from a three-dimensional surface shape in a predetermined region. Therefore, for example, in cases such as when there are depressed portions at predetermined intervals on the surface, it is possible to determine the shape of the surface with accuracy because the arithmetic mean roughness Sa varies little from measurement to measurement.

The material composing the skin substitute membrane of this embodiment is not limited in particular if its spectral transmittance for light of 290 nm to 400 nm in wavelength is 50% to 100%, and may be resin such as polymethylmethacrylate (PMMA), polyethylene (PE), or nylon. PMMA is preferable because of its superiority in spectral transmittance for light of 290 nm to 400 nm in wavelength. (See FIG. 1.) FIG. 1 also illustrates the results of quartz and VITRO-SKIN (registered trademark), where quartz, PMMA, PE, and nylon are 3 mm, 3 mm, 0.2 mm, and 0.5 mm, respectively, in thickness. Of these, quartz is not optimum from a comprehensive perspective because quartz, whose surface is hydrophilic, cannot fully replicate skin having a hydrophobic surface, although quartz has an excellent ultraviolet radiation transmission characteristic.

The thickness of the skin substitute membrane of this embodiment is not limited in particular, and is preferably 0.1 mm to 5 mm, and more preferably, 0.2 mm to 3 mm. If the thickness is less than 0.1 mm, the skin substitute membrane is fragile and breaks easily. Therefore, it may be difficult to manufacture the skin substitute membrane with stability. If the thickness exceeds 5 mm, the spectral transmittance of the skin substitute membrane for light of 290 nm to 400 nm in wavelength may be less than 50%.

The method of providing surface roughness in manufacturing the skin substitute membrane of this embodiment is not limited in particular if the method is capable of causing the arithmetic mean roughness Sa of the surface to be 13 µm to 30 µm, and may be sandblasting, molding, laser processing or the like, of which two or more may be used together.

Commercially-available PMMA plates used in the case of sandblasting include SUMIPEX 010 (manufactured by Sumitomo Chemical Co., Ltd.), PARAGLAS UV00 (manufactured by KURARAY Co., Ltd.), and ACRYLITE 000 (manufactured by Mitsubishi Rayon Co., Ltd.). Further, commercially-available products of material PMMA used in the case of molding include ACRYPET VH000 (manufactured by Mitsubishi Rayon Co., Ltd.).

The material composing a mold used in the case of molding is not limited in particular, and may be metal such as aluminum, nickel, or copper; resin such as acrylic resin or epoxy resin; a mixture of metallic powder and resin (metal resin), or the like.

The mold may be manufactured using a master manufactured by machining. The material composing the master is not limited in particular, and may be metal such as aluminum, nickel, or copper; resin such as acrylic resin or epoxy resin; a mixture of metallic powder and resin (metal resin), or the like.

The method of roughening the surface of the mold is not limited in particular, and may be transferring a master whose surface is roughened by sandblasting, providing roughness by performing sandblasting directly on the surface of the mold, or the like.

Figure 2:
FIG. 2 is a cross-sectional view illustrating a mold having a surface with chamfered roughness.
Figure 3:
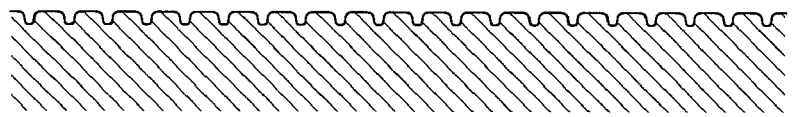
FIG. 3 is a cross-sectional view illustrating a skin substitute membrane having a surface with chamfered roughness.

In the case of using a mold whose surface is provided with chamfered roughness (see FIG. 2), a skin substitute membrane whose surface is provided with chamfered roughness (see FIG. 3) is obtained. With respect to such a skin substitute membrane, which has a high spectral transmittance for light of 290 nm to 400 nm in wavelength, the difference in a spectral transmittance for light of 300 nm in wavelength between before and after application of 1 mg/cm$^2$ of glycerin is preferably less than 5%. This reduces variations in measuring the ultraviolet radiation transmission characteristic and/or reflection characteristic of an external preparation for skin. As a result, it is possible to measure the ultraviolet radiation transmission characteristic and/or reflection characteristic of the external preparation for skin with more accuracy.

Second Embodiment

The surface of one side of a skin substitute membrane of this embodiment includes groove-shaped depressed portions whose cross sections have a chamfered V-letter shape and planar portions, and has an arithmetic mean roughness Sa of 10 µm to 50 µm, preferably 10 µm to 30 µm. Further, the depressed portions are 50 µm to 500 µm, preferably 200 µm to 400 µm, in width. Further, the depressed portions are 30 µm to 150 µm, preferably 50 µm to 100 µm, in depth. Further, the skin substitute membrane of this embodiment has a spectral transmittance of 50% to 100%, more preferably 60% to 100%, for light of 290 nm to 400 nm in wavelength. As a result, a skin substitute membrane is obtained that makes it possible to measure the ultraviolet radiation transmission characteristic and/or reflection characteristic of an external preparation for skin with accuracy. Such a skin substitute membrane allows reproduction of the amount of application of an external preparation for skin in measuring in vivo SPFs determined in Non-Patent Document 3, which is 2.00 mg/cm², while facilitating even application of the external preparation for skin. Therefore, such a skin substitute membrane is particularly effective in reproducing a phenomenon on skin in measuring in vivo SPFs in the case of evaluating the estimated in vitro SPFs of an external preparation for skin subject to degradation due to ultraviolet radiation.

At this point, if the arithmetic mean roughness Sa of the surface of the skin substitute membrane is less than 10 μm, it becomes difficult to evenly apply 2.00 mg/cm² of the external preparation for skin. On the other hand, if the arithmetic mean roughness Sa of the surface of the skin substitute membrane exceeds 50 μm, the difference from the shape of the surface of skin increases. Therefore, even if the amount of application in evaluating the external preparation for skin is caused to be 2.00 mg/cm², it is difficult to reproduce conditions in evaluating the external preparation for skin in vivo, such as the condition of application of the external preparation for skin at a microscopic level and an attenuation pattern in the case of degradation due to ultraviolet radiation.

Further, if the depressed portions are less than 50 μm in width, the applied external preparation for skin does not spread all over the depressed portions, and if the depressed portions exceed 500 μm in width, the applied external preparation for skin concentrates on the depressed portions. Likewise, if the depressed portions are less than 30 μm in depth, the applied external preparation for skin does not spread all over the depressed portions, and if the depressed portions exceed 150 μm in depth, the applied external preparation for skin concentrates on the depressed portions.

Further, if the spectral transmittance of the skin substitute film for light of 290 nm to 400 nm in wavelength is less than 50%, the accuracy of the ultraviolet radiation transmission characteristic and/or reflection characteristic of the external preparation for skin is insufficient.

In the skin substitute membrane of this embodiment, the arithmetic mean roughness Sa of the planar portions is preferably 0.1 μm to 30 μm. If the arithmetic mean roughness Sa of the planar portions is less than 0.1 μm, the applied external preparation for skin may not adhere to the planar portions. If the arithmetic mean roughness Sa of the planar portions exceeds 30 μm, the applied external preparation for skin may not adhere evenly to the planar portions.

With respect to the skin substitute membrane of this embodiment, which has a high spectral transmittance for light of 290 nm to 400 nm in wavelength because the depressed portions are chamfered, the difference in a spectral transmittance for light of 300 nm in wavelength between before and after application of 1 mg/cm² of glycerin is preferably less than 5%. This reduces variations in measuring the ultraviolet radiation transmission characteristic and/or reflection characteristic of an external preparation for skin. As a result, it is possible to measure the ultraviolet radiation transmission characteristic and/or reflection characteristic of the external preparation for skin with more accuracy.

The material composing the skin substitute membrane of this embodiment is not limited in particular if its spectral transmittance for light of 290 nm to 400 nm in wavelength is 50% to 100%, and may be resin such as polymethylmethacrylate (PMMA), polyethylene (PE), or nylon. PMMA is preferable because of its superiority in spectral transmittance for light of 290 nm to 400 nm in wavelength.

Commercially-available products of PMMA include ACRYPET VH000 (manufactured by Mitsubishi Rayon Co., Ltd.).

The thickness of the skin substitute membrane of this embodiment is not limited in particular, and is preferably 0.1 mm to 5 mm, and more preferably, 2 mm to 3 mm. If the thickness is less than 0.1 mm, the skin substitute membrane is fragile and breaks easily. Therefore, it may be difficult to manufacture the skin substitute membrane with stability. If the thickness exceeds 5 mm, the spectral transmittance of the skin substitute membrane for light of 290 nm to 400 nm in wavelength may be less than 50%.

The method of manufacturing the skin substitute membrane of this embodiment is not limited in particular, and may be molding, a combination of molding and sandblasting, or the like.

A mold used in the case of molding has a recess corresponding to the skin substitute membrane of this embodiment formed on the surface of one side. Further, at the bottom surface of the recess of the mold, projecting portions whose cross sections have a chamfered inverse V-letter shape to correspond to the depressed portions of the skin substitute membrane of this embodiment and planar portions corresponding to the planar portions of the skin substitute membrane of this embodiment are formed. Here, the arithmetic mean roughness Sa of the surface of the recess of the mold, which is substantially the same as the arithmetic mean roughness Sa of the surface of the skin substitute membrane of this embodiment, is 10 μm to 50 μm, preferably 10 μm to 30 μm. Further, the width of the projecting portions of the mold, which is substantially the same as the width of the depressed portions of the skin substitute membrane of this embodiment, is 50 μm to 500 μm, preferably 200 μm to 400 μm. Further, the height of the projecting portions of the mold, which is substantially the same as the depth of the depressed portions of the skin substitute membrane of this embodiment, is 30 μm to 150 μm, preferably 50 μm to 100 μm.

Further, the arithmetic mean roughness Sa of the planar portions of the mold, which is substantially the same as the arithmetic mean roughness Sa of the planar portions of the skin substitute membrane of this embodiment, is preferably 0.1 μm to 30 μm.

The material composing the mold is not limited in particular, and may be metal such as nickel, aluminum, or copper; resin such as acrylic resin or epoxy resin; a mixture of metallic powder and resin (metal resin), or the like.

The mold may be manufactured using a master manufactured by machining. The material composing the master is not limited in particular, and may be metal such as nickel, aluminum, or copper; resin such as acrylic resin or epoxy resin; a mixture of metallic powder and resin (metal resin), or the like.

The method of roughening the planar portions of the mold is not limited in particular, and may be transferring a master whose surface is roughened by sandblasting, roughening the surface of the mold by sandblasting, or the like.

Instead of using a mold having roughened planar portions, the planar portions of the skin substitute membrane of this embodiment may be roughened by performing sandblasting after molding using a mold whose planar portions are not roughened.

Figure 4A:
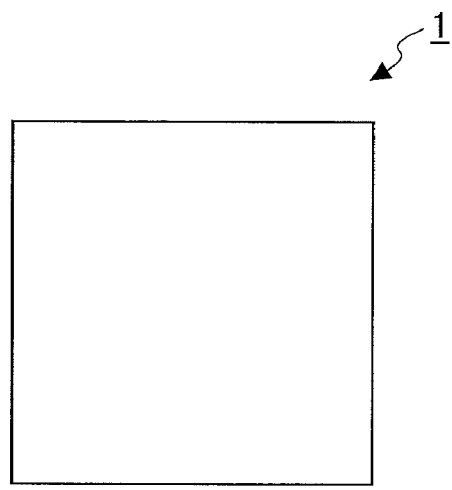
FIG. 4A is a plan view illustrating a skin substitute membrane of a second embodiment of the present invention.
Figure 4B:
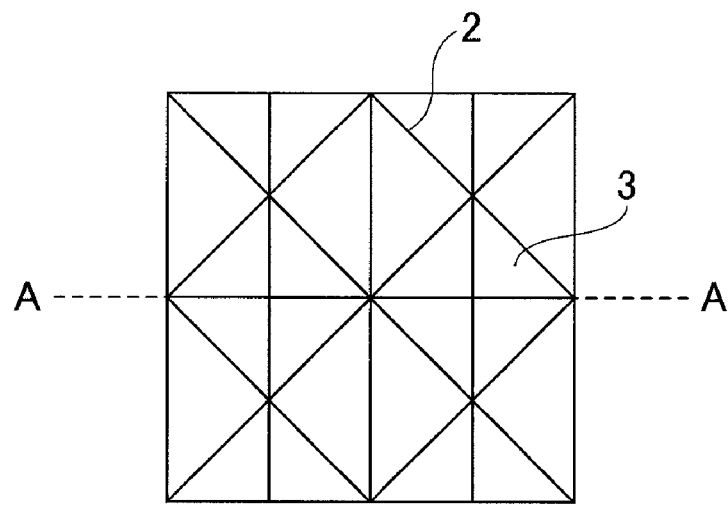
FIG. 4B is an enlarged view of part of the skin substitute membrane of FIG. 4A.
Figure 4C:
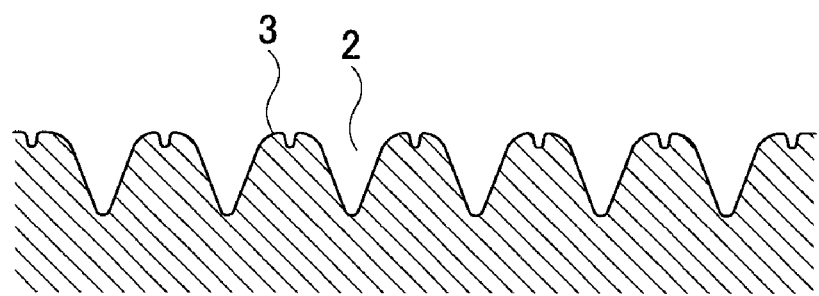
FIG. 4C is a cross-sectional view taken along A-A direction of FIG. 4B.

FIG. 4A illustrates an example of the skin substitute membrane of this embodiment. The surface of one side of a skin substitute membrane 1 includes groove-shaped depressed portions 2 whose cross sections have a chamfered V-letter shape and planar portions 3 as illustrated in FIG. 4B and FIG. 4C, and has an arithmetic mean roughness Sa of 10 μm to 50 μm. The depressed portions 2 are 50 μm to 500 μm in width and 30 μm to 150 μm in depth. The frequency of one crossing another of the depressed portions 2 is 0.1 portions/mm to 2.0 portions/mm. Further, the planar portions 3 have an arithmetic mean roughness Sa of 0.1 μm to 30 μm, and are provided with chamfered roughness. The skin substitute membrane 1 is formed by molding.

The groove-shaped depressed portions 2 whose cross sections have a chamfered V-letter shape are formed and the planar portions 3 are provided with chamfered roughness in the skin substitute membrane 1. Therefore, the spectral transmittance for light of 290 nm to 400 nm in wavelength is high, and the difference in a spectral transmittance for light of 300 nm in wavelength between before and after application of 1 mg/cm$^2$ of glycerin is less than 5%. This makes it possible to measure the ultraviolet radiation transmission characteristic and/or reflection characteristic of an external preparation for skin with more accuracy.

The shape and the structure of the cross sections of the depressed portions of the skin substitute membrane are not limited in particular as long as the shape and the structure allow even application of an external preparation for skin.

Figure 5A:
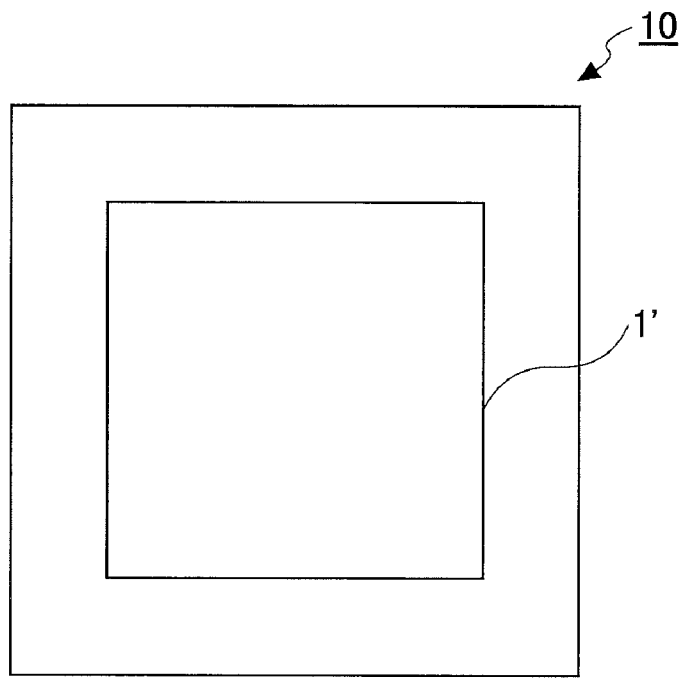
FIG. 5A is a plan view illustrating a mold used in manufacturing the skin substitute membrane of FIG. 4A.
Figure 5B:
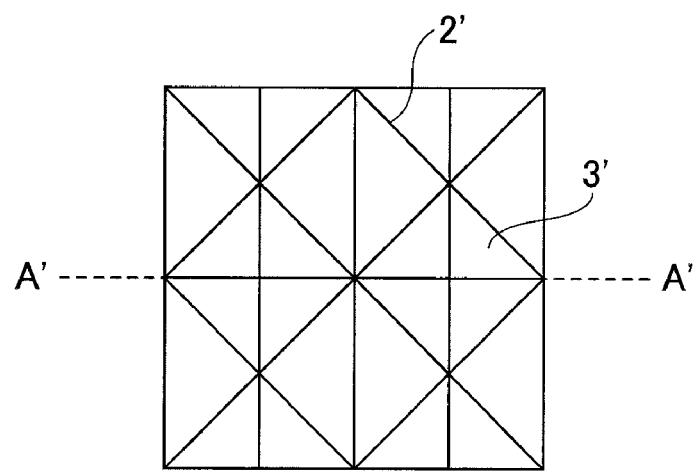
FIG. 5B is an enlarged view of part of a bottom surface of a recess of the mold of FIG. 5A.
Figure 5C:
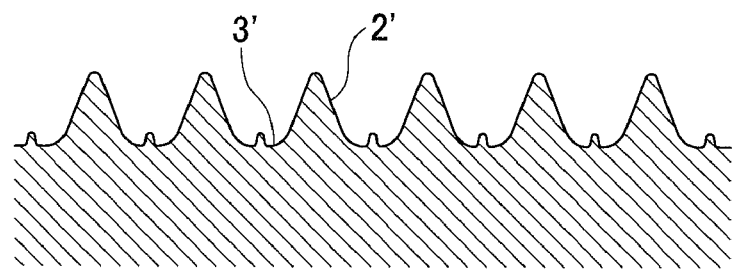
FIG. 5C is a cross-sectional view taken along A-A direction of FIG. 5B.

FIG. 5A illustrates a mold used in manufacturing the skin substitute membrane 1. A mold 10 has a recess 1' formed on the surface of one side. Further, projecting portions 2' whose cross sections have a chamfered inverse V-letter shape and planar portions 3' are formed at the bottom surface of the recess 1' as illustrated in FIG. 5B and FIG. 5C. Here, the arithmetic mean roughness Sa of the surface of the recess 1' is 10 µm to 50 µm. Further, the projecting portions 2' are 50 µm to 500 µm in width and 30 µm to 150 µm in height. Further, the frequency of one crossing another of the projecting portions 2' is 0.1 to 2 portions per millimeter. Further, the planar portions 3' have an arithmetic mean roughness Sa of 0.1 µm to 30 µm, and are provided with chamfered roughness.

The shape and the structure of the cross sections of the projecting portions of the mold are not limited in particular as long as the shape and the structure allow manufacture of a skin substitute membrane that allows even application of an external preparation for skin.

Third Embodiment

A method of evaluating an external preparation for skin of this embodiment includes the process of applying the external preparation for skin on the skin substitute membrane of the first embodiment or the second embodiment of the present' invention and the process of evaluating the ultraviolet radiation transmission characteristic and/or reflection characteristic of the external preparation for skin by exposing the skin substitute membrane on which the external preparation for skin is applied to light containing ultraviolet radiation.

Here, the amount of application of the external preparation for skin is preferably 1.20 mg/cm$^2$ to 2.40 mg/cm$^2$. This makes it possible to measure the ultraviolet radiation transmission characteristic and/or reflection characteristic of the external preparation for skin with accuracy.

External preparations for skin are not limited in particular, and include sunscreen cosmetics, makeup cosmetics, skin-care cosmetics, pre-makeup cosmetics, and body cosmetics. Further, forms of external preparations for skin are not limited in particular, and include emulsion, lotion, a solid, oil, and spray.

Further, the method of applying an external preparation for skin on the skin substitute membrane is not limited in particular, and may be application with a finger, application with a finger with a fingerstall, etc., based on the specifications in the case of performing measurement in vivo.

The apparatus for measuring the ultraviolet radiation transmission characteristic and/or reflection characteristic of an external preparation for skin is not limited in particular, and evaluation apparatuses disclosed in Japanese Laid-Open Patent Application No. 2008-96151 and Japanese Laid-Open Patent Application No. 2008-111834 may be used.

Figure 6:
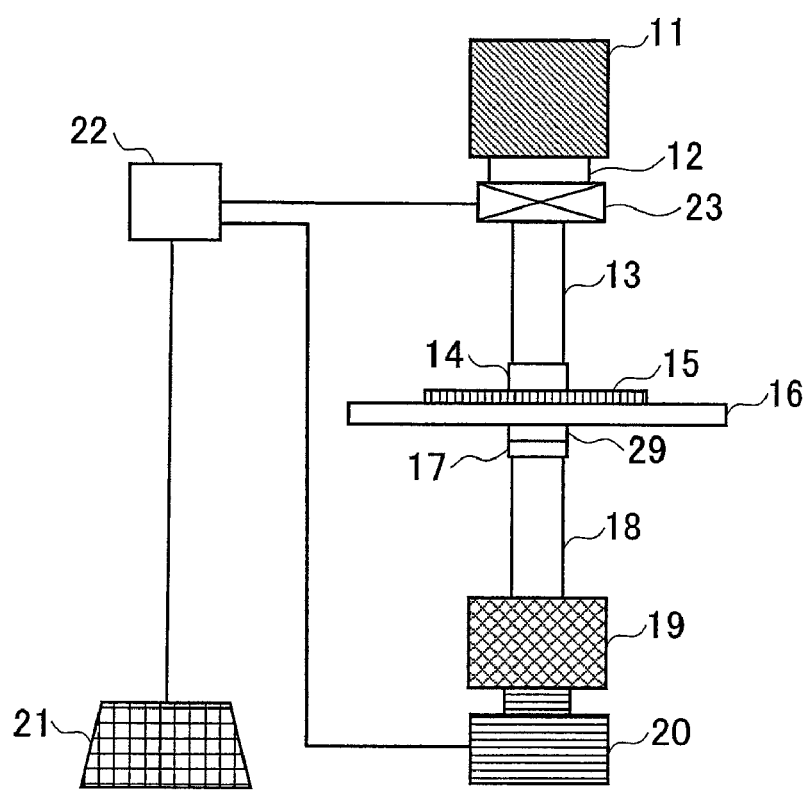
FIG. 6 is a diagram illustrating an apparatus for evaluating the ultraviolet radiation transmission characteristic of an external preparation for skin used in a third embodiment of the present invention.

FIG. 6 illustrates an example of the apparatus for evaluating the ultraviolet radiation transmission characteristic of an external preparation for skin used in this embodiment. An evaluation apparatus 10 includes a light source 11, a filter 12, a light chopper 23, an optical fiber 13, an irradiation port 14, a skin substitute membrane 16 on which an external preparation for skin 15 is applied, an integrating sphere 29, a detection port 17, an optical fiber 18, a spectrometer 19, a photodetector 20, an electrical signal processing and analyzing unit (a computer 21), and a lock-in amplifier 22. The skin substitute membrane 16 may be placed on a substrate of quartz or the like having an excellent ultraviolet radiation transmission characteristic as required.

The light source 11 is not limited in particular, and a xenon lamp, which is a white light source including ultraviolet radiation, visible radiation, and infrared radiation, or the like may be used. The white light emitted from the xenon lamp may be used as simulated sunlight.

The filter 12, which is in the vicinity of the light source 11 in the traveling direction of the light emitted from the light source 11, corrects the light emitted from the light source 11 to ultraviolet radiation (for example, ultraviolet radiation of 290 nm to 400 nm in wavelength), so that the light chopper 23 is exposed to the ultraviolet radiation passing through the filter 12. The filter 12 is not limited in particular, and may be a WG320 or a UG11 (manufactured by SCHOTT) or the like.

The light chopper 23, which is a shutter that intermittently transmits the ultraviolet radiation passing through the filter 12, emits the ultraviolet radiation in pulses. The ultraviolet radiation is emitted in pulses to the optical fiber 13.

Further, the light chopper 23 is connected to the lock-in amplifier 22 with an electrical interconnection, and obtains the synchronization signal of the pulsed light from the lock-in amplifier 22 to perform synchronization analysis on a signal from the photodetector 20.

The optical fiber 13, which is in the vicinity of the light chopper 23 in the traveling direction of the ultraviolet radiation emitted from the light chopper 23, guides the ultraviolet radiation to the irradiation port 14. The skin substitute membrane 16 on which the external preparation for skin 15 is applied is exposed to the ultraviolet radiation guided to the irradiation port 14.

The irradiation port 14 and the detection port 17 are fixed at a predetermined interval, and the skin substitute membrane 16 on which the external preparation for skin 15 is applied is fixed at a certain distance from the irradiation port 14. Here, the irradiation port 14, the external preparation for skin 15, the skin substitute membrane 16, and the integrating sphere 29 are arranged in this order relative to the traveling direction of the ultraviolet radiation.

The integrating sphere 29 receives the ultraviolet radiation passing through the external preparation for skin 15 and the skin substitute membrane 16, concentrates the ultraviolet radiation, and makes the ultraviolet radiation uniform by spatially integrating the ultraviolet radiation. The integrating sphere 29 may be omitted.

The detection port 17 receives the ultraviolet radiation made uniform by the integrating sphere 29, and guides the ultraviolet radiation to the optical fiber 18.

The optical fiber 18, which is in the vicinity of the detection port 17 in the traveling direction of the ultraviolet radiation emitted from the detection port 17, guides the ultraviolet radiation received by the detection port 17 to the spectrometer 19.

The spectrometer 19 is light splitting means for spectrally splitting the ultraviolet radiation emitted from the optical fiber 18 at intervals of 1 nm in a 290 nm to 400 nm range. The photodetector 20 is exposed to the ultraviolet radiation spectrally split by the spectrometer 19.

The spectrometer 19, which has its sensitivity characteristic adjusted to ultraviolet radiation, may realize a highly sensitive spectral performance by using a diffraction grating having a good sensitivity characteristic in a wavelength range of 290 nm to 400 nm in particular. Such a diffraction grating is not limited in particular, and may be a concave diffraction grating (model number 10-015) (manufactured by Shimadzu Corporation) or the like.

The photodetector 20 detects the ultraviolet radiation spectrally split by the spectrometer 19 with an optical sensor, and converts the intensity of a light beam of each wavelength into a current or voltage signal. This current or voltage signal is transmitted to the computer 21 connected to the photodetector 20 with an electrical interconnection.

The photodetector 20, which has its sensitivity characteristic adjusted to ultraviolet radiation, may have improved sensitivity for detecting ultraviolet radiation by employing a photomultiplier having a good sensitivity characteristic in a wavelength range of 290 nm to 400 nm in particular. Such a photomultiplier is not limited in particular, and may be one having a photoelectric surface formed of In, Ga, N, Al, O, Cs, etc., specifically, an InGaN photoelectric surface.

Further, a semiconductor photodetector formed of In, Ga, N, Al, O, etc., also may be used as the photodetector 20.

The computer 21, which is connected to the lock-in amplifier 22 with an electrical interconnection, receives data after detection of a signal received from the photodetector 20 in the lock-in amplifier 22, and processes the data so that the data are easily understandable by a user of the evaluation apparatus 10 to allow results to be displayed on a screen, printed out on recording paper, or stored in a storage medium.

A general-purpose personal computer or the like may be used as the computer 21, which is capable of causing functions of the evaluation apparatus 10 to be executed based on instructions from a user through input means or the like.

The lock-in amplifier 22 is connected to the photodetector 20, the computer 21, and the light chopper 23 with electrical interconnections. The lock-in amplifier 22 performs control so as to synchronize the pulsed light emitted from the light chopper 23 and a signal received from the photodetector 20. Specifically, the two signals are synchronized using a phase detector circuit in the lock-in amplifier 22.

The arrangement of the means may be changed inside the evaluation apparatus 10 as required.

The method of evaluating the ultraviolet radiation transmission characteristic of an external preparation for skin is not limited in particular, and the in vitro SPF evaluation methods disclosed in Japanese Patent No. 3337832 and Japanese Laid-Open Patent Application No. 2008-111834 may be used. This makes it possible to measure estimated in vitro SPFs.

Methods of evaluating the ultraviolet radiation transmission characteristic and/or reflection characteristic of an external preparation for skin other than these include an in vitro UVA evaluation method, an in vitro PPD method, an in vitro PFA method, an in vitro UVA PF method, a critical wavelength method, a UVA/UVB ratio method, an Australian/New Zealand method, a German DIN UVA balance method, and an SPF/UVA PF (PPD) ratio method, of which two or more may be used together. (See Ferrero, L. et al.; "Importance of Substrate Roughness for In Vitro Sun Protection Assessment," IFSCC Magazine, Vol. 9, No. 2, 97-108 (2006)).

EXAMPLES

Example 1-1

The surface of a PMMA plate (manufactured by Sumitomo Chemical Co., Ltd.) was sprayed with FUJIRANDOM WA#16 (manufactured by Fuji Manufacturing Co., Ltd.), which is a fused white alumina abrasive, and was subjected to sandblasting using a sand blaster PNEUMA BLASTER (manufactured by Fuji Manufacturing Co., Ltd.). Thereafter, the PMMA plate was cut to be 50 mm square, thereby manufacturing a skin substitute membrane. The arithmetic mean roughness Sa of the surface of the skin substitute membrane, which was measured using a confocal microscope (manufactured by Lasertech Corporation), was 15 μm.

Examples 1-2 and 1-3, Comparative Examples 1 to 3

Skin substitute membranes were manufactured the same as in Example 1-1 except for changing the sandblasting time, and the arithmetic mean roughness Sa was measured for the surfaces of the skin substitute membranes. (See Table 1.)

Reference Example 1

A replica was taken from a homogeneous portion of a human back using a commercially-available replica material, and the arithmetic mean roughness Sa of the surface of the replica was measured the same as in Example 1-1. (See Table 1.)

In selecting [Optimum Amount Of Application Of External Preparation For Skin], an external preparation for skin was applied to the surface of the homogeneous portion of the human back.

[Optimum Amount of Application of External Preparation for Skin]

A predetermined amount of an external preparation for skin was applied on the surfaces of the skin substitute membranes of Examples and Comparative Examples and the surface of the skin of Reference Example by ten cosmetics specialists applying and spreading the external preparation for skin with their fingers for one minute. Thereafter, they were dried at 25° C. for 15 minutes, and apparent uniformity was evaluated. As the external preparation for skin, a preparation containing titanium oxide was used in order to make it easier to determine unevenness of application or the like. Further, the apparent uniformity was evaluated in a room where an environment with a certain amount of lighting was prepared, with black paper being laid underneath. The evaluation results are shown in Table 1.

TABLE 1

| | ARITHMETIC MEAN ROUGHNESS Sa OF SURFACE OF SKIN SUBSTITUTE MEMBRANE [μm] | APPLICATION AMOUNT OF EXTERNAL PREPARATION FOR SKIN [mg/cm$^2$] | | | | | |
|---|---|---|---|---|---|---|---|
| | | 0.50 | 0.75 | 1.00 | 1.20 | 1.40 | 2.00 |
| EXAMPLE 1-1 | 15 | X | X | Δ | ○ | ○ | ◎ |
| EXAMPLE 1-2 | 20 | X | X | Δ | ○ | ○ | ◎ |
| EXAMPLE 1-3 | 25 | X | X | Δ | ○ | ○ | ◎ |
| COMPARATIVE EXAMPLE 1 | 2 | ○ | ◎ | ○ | X | X | X |
| COMPARATIVE EXAMPLE 2 | 6 | X | Δ | ○ | ◎ | ○ | Δ |
| COMPARATIVE EXAMPLE 3 | 12 | X | X | Δ | ○ | ◎ | Δ |
| REFERENCE EXAMPLE 1 | 20 | X | X | Δ | ○ | ○ | ◎ |

The apparent uniformity was scored with 1 for non-uniform appearance, 2 for slightly non-uniform appearance, 3 for neither non-uniform nor uniform appearance, 4 for slightly uniform appearance, and 5 for uniform appearance, and was determined as x if the average was more than or equal to 1 and less than 2, as Δ if the average is more than or equal to 2 and less than 3, as ○ if the average was more than or equal to 3 and less than 4, and as ◎ if the average was more than or equal to 4.

As a result, it has been found that the optimum amount of application of an external preparation for skin is 2.00 mg/cm$^2$ for the skin substitute membranes of the Examples, whose surfaces have arithmetic mean roughness Sa approximated to that of skin, and the skin of Reference Example. On the other hand, it has been found that the optimum amount of application is 0.75, 1.20, and 1.40 for the skin substitute membranes of Comparative Examples 1 to 3, respectively.

[Correlation Between Estimated In Vitro SPF and In Vivo SPF]

Figure 7:
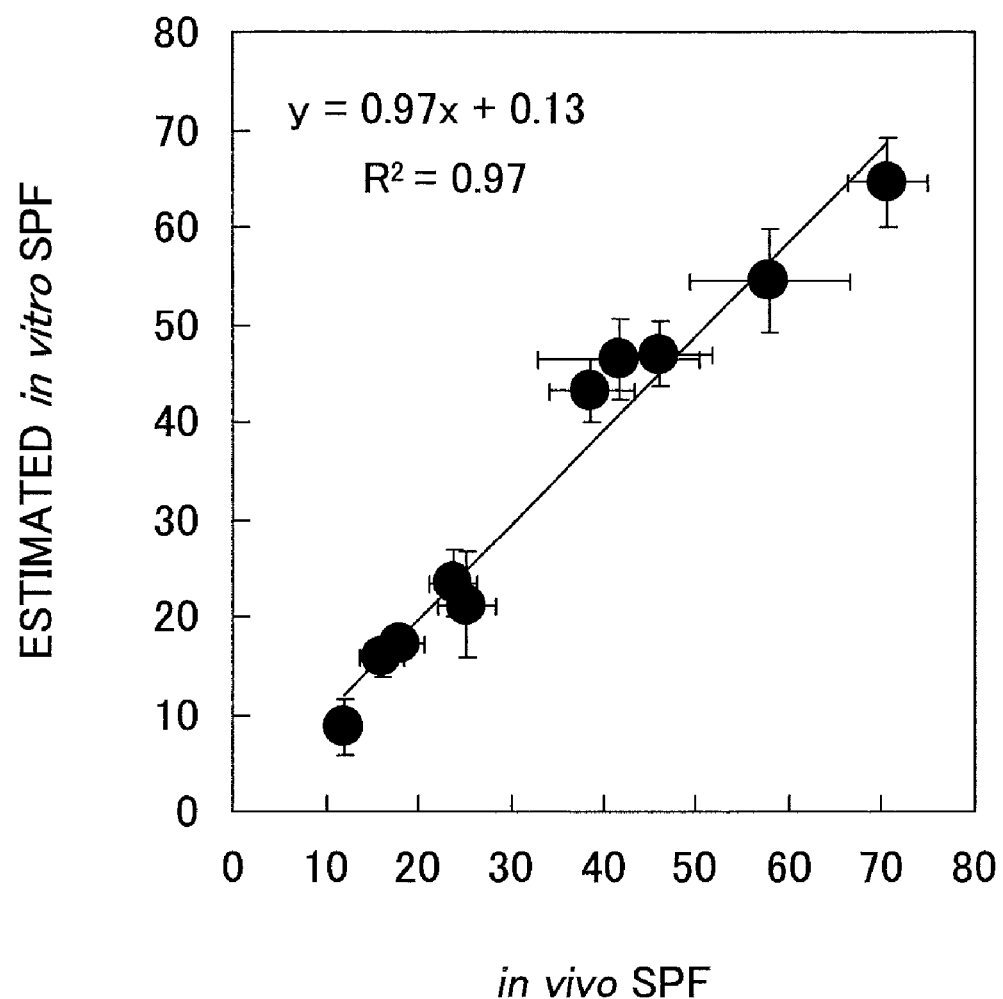
FIG. 7 is a graph illustrating the results of measurement of estimated in vitro SPFs using the skin substitute membrane of the second embodiment.

Ten kinds of external preparations for skin having predetermined in vivo SPFs (see FIG. 7) were prepared. The optimum amount of an external preparation for skin was applied on the skin substitute membranes of Example 1-2 and Comparative Examples 1 and 2 by applying and spreading the external preparation for skin with a finger for one minute. Thereafter, they were dried at 25° C. for 15 minutes. Next, estimated in vitro SPFs were measured according to the in vitro SPF evaluation method disclosed in Example 1 of Japanese Laid-Open Patent Application No. 2008-111834 using the ultraviolet radiation transmission characteristic evaluation apparatus 10 illustrated in FIG. 6, and the coefficient of correlation with the in vivo SPFs R$^2$ and the gradient a of the approximation expression were determined. (See FIG. 7.) The results are shown in Table 2.

Table 2 shows that in the case of using the skin substitute membrane of Example 2, the coefficient of correlation R$^2$ is closer to one and the gradient a of the approximation expression is closer to one than in the case of using the skin substitute membranes of Comparative Examples 1 and 2, so that the estimated in vitro SPFs reproduce the in vivo SPF with high accuracy.

Example 2-1

Figure 8:
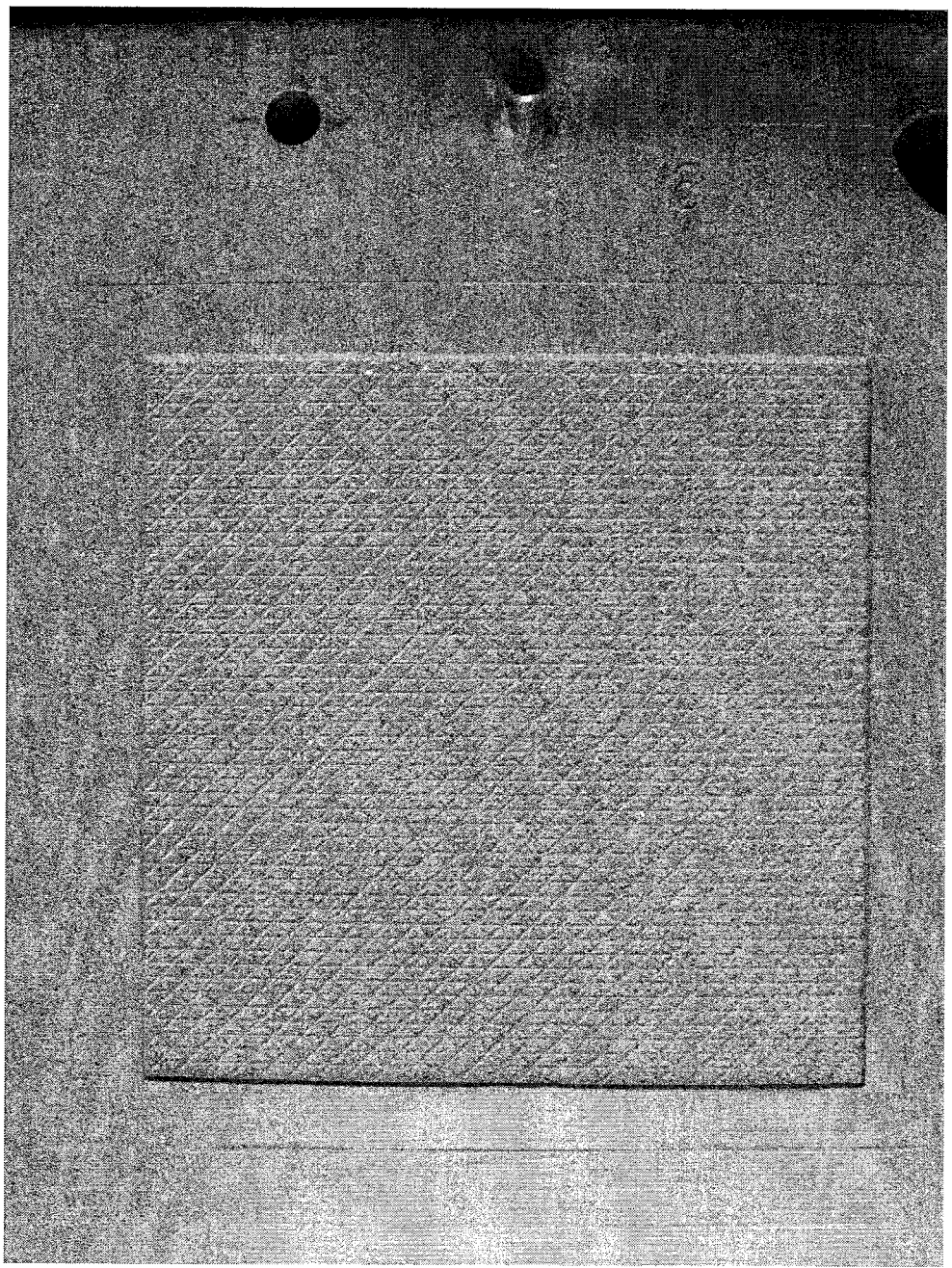
FIG. 8 is a photograph of a bottom surface of a second mold used in Example 2-1.
Figure 9:
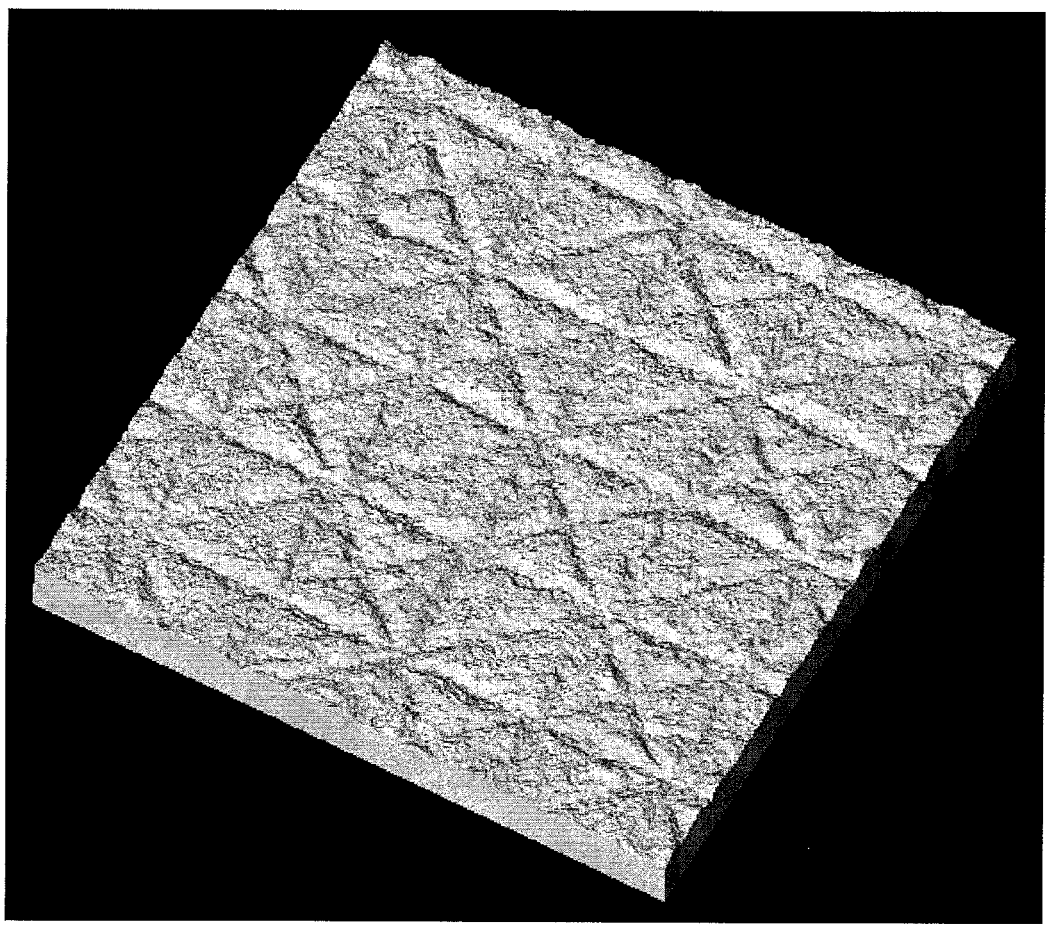
FIG. 9 is a confocal microscope photograph of a skin substitute membrane of Example 2-1.

A copper plate (steel material) was subjected to machining so that groove-shaped depressed portions with V-shaped cross sections, 300 μm in width and 80 μm in depth, were formed one/2 mm vertically, one/1 mm laterally, and two/3 mm in a 45° oblique direction, thereby manufacturing a first master of 50 mm square. A first mold was manufactured by performing nickel electrocasting with the first master. ACRYPET VH000 (manufactured by Mitsubishi Rayon Co., Ltd.) as PMMA was molded by injection molding using the first mold. The surface of the obtained molded article on the side on which groove-shaped depressed portions were formed was sprayed with FUJIRANDOM WA#80 (manufactured by Fuji Manufacturing Co., Ltd.), which is a fused white alumina abrasive, and was subjected to sandblasting using a sand blaster PNEUMA BLASTER (manufactured by Fuji Manufacturing Co., Ltd.), thereby manufacturing a second master. Metal resin was molded using the second master, thereby manufacturing a second mold with chamfered projecting portions and planar portions provided with chamfered roughness. (See FIG. 8.) A skin substitute membrane was manufactured by molding ACRYPET VH000 (manufactured by Mitsubishi Rayon Co., Ltd.) by injection molding using the second mold. (See FIG. 9.)

TABLE 2

| | ARITHMETIC MEAN ROUGHNESS Sa OF SURFACE OF SKIN SUBSTITUTE MEMBRANE [μm] | APPLICATION AMOUNT OF EXTERNAL PREPARATION FOR SKIN [mg/cm$^2$] | GRADIENT a OF APPROXIMATION EXPRESSION | COEFFICIENT OF CORRELATION R$^2$ |
|---|---|---|---|---|
| EXAMPLE 1-2 | 20 | 2.00 | 0.97 | 0.97 |
| COMPARATIVE EXAMPLE 1 | 2 | 0.75 | 0.78 | 0.83 |
| COMPARATIVE EXAMPLE 2 | 6 | 1.20 | 0.83 | 0.91 |

Example 2-2

A skin substitute membrane was manufactured the same as in Example 2-1 except that the groove-shaped depressed portions of the first master were 250 μm in width and 70 μm in depth and that FUJIRANDOM WA#60 (manufactured by Fuji Manufacturing Co., Ltd.), which is a fused white alumina abrasive, was used in sandblasting.

Example 2-3

A skin substitute membrane was manufactured the same as in Example 2-1 except that the groove-shaped depressed portions of the first master were 400 μm in width and 100 μm in depth and that FUJIRANDOM WA#100 (manufactured by Fuji Manufacturing Co., Ltd.), which is a fused white alumina abrasive, was used in sandblasting.

Example 2-4

A skin substitute membrane was manufactured the same as in Example 2-1 except that the groove-shaped depressed portions of the first master were 200 μm in width and 60 μm in depth and that FUJIRANDOM WA#30 (manufactured by Fuji Manufacturing Co., Ltd.), which is a fused white alumina abrasive, was used in sandblasting.

Example 2-5

A copper plate (steel material) was subjected to machining so that groove-shaped depressed portions with V-shaped cross sections, 300 μm in width and 80 μm in depth, were formed one/2 mm vertically, one/1 mm laterally, and two/3 mm in a 45° oblique direction, thereby manufacturing a master of 50 mm square. After performing nickel electrocasting with the master, the surface on the side on which projecting portions were formed was sprayed with FUJIRANDOM WA#80 (manufactured by Fuji Manufacturing Co., Ltd.), which is a fused white alumina abrasive, and was subjected to sandblasting using a sand blaster PNEUMA BLASTER (manufactured by Fuji Manufacturing Co., Ltd.), thereby manufacturing a mold with chamfered projecting portions and planar portions provided with non-chamfered roughness. A skin substitute membrane was manufactured by molding ACRYPET VH000 (manufactured by Mitsubishi Rayon Co., Ltd.) by injection molding using the mold.

Example 2-6

A copper plate (steel material) was subjected to machining so that groove-shaped depressed portions with V-shaped cross sections, 300 μm in width and 80 μm in depth, were formed one/2 mm vertically, one/1 mm laterally, and two/3 mm in a 45° oblique direction, thereby manufacturing a master of 50 mm square. A mold with chamfered projecting portions was manufactured by performing nickel electrocasting with the master. ACRYPET VH000 (manufactured by Mitsubishi Rayon Co., Ltd.) was molded by injection molding using the mold. The surface of the obtained molded article on the side on which groove-shaped depressed portions were formed was sprayed with FUJIRANDOM WA#80 (manufactured by Fuji Manufacturing Co., Ltd.), which is a fused white alumina abrasive, and was subjected to sandblasting using a sand blaster PNEUMA BLASTER (manufactured by Fuji Manufacturing Co., Ltd.), thereby manufacturing a skin substitute membrane.

Example 2-7

A skin substitute membrane was manufactured the same as in Example 2-6 except that FUJIRANDOM WA#100 (manufactured by Fuji Manufacturing Co., Ltd.), which is a fused white alumina abrasive, was used in sandblasting.

Example 2-8

A skin substitute membrane was manufactured the same as in Example 2-6 except that no sandblasting was performed.

Example 1-4

The surface of one side of ACRYLITE 000 (manufactured by Mitsubishi Rayon Co., Ltd.) as a PMMA plate is sprayed with FUJIRANDOM WA#16 (manufactured by Fuji Manufacturing Co., Ltd.), which is a fused white alumina abrasive, and was subjected to sandblasting using a sand blaster PNEUMA BLASTER (manufactured by Fuji Manufacturing Co., Ltd.), thereby manufacturing a master of 50 mm square. A mold having a surface provided with chamfered roughness was manufactured by performing nickel electrocasting with the master. ACRYPET VH000 (manufactured by Mitsubishi Rayon Co., Ltd.) was molded by injection molding using the mold, thereby manufacturing a skin substitute membrane.

Comparative Example 4

A skin substitute membrane was manufactured the same as in Example 1-4 except that FUJIRANDOM WA#100 (manufactured by Fuji Manufacturing Co., Ltd.), which is a fused white alumina abrasive, was used in sandblasting.

Comparative Example 5

A skin substitute membrane was manufactured the same as in Example 1-4 except that FUJIRANDOM WA#60 (manufactured by Fuji Manufacturing Co., Ltd.), which is a fused white alumina abrasive, was used in sandblasting.

Example 1-5

The surface of one side of a copper plate (steel material) was sprayed with FUJIRANDOM WA#16 (manufactured by Fuji Manufacturing Co., Ltd.), which is a fused white alumina abrasive, and was subjected to sandblasting using a sand blaster PNEUMA BLASTER (manufactured by Fuji Manufacturing Co., Ltd.), thereby manufacturing a mold. ACRYPET VH000 (manufactured by Mitsubishi Rayon Co., Ltd.) was molded by injection molding using the mold and was thereafter cut to be 50 mm square, thereby manufacturing a skin substitute membrane.

Comparative Example 6

A skin substitute membrane was manufactured the same as in Example 1-5 except that FUJIRANDOM WA#100 (manufactured by Fuji Manufacturing Co., Ltd.), which is a fused white alumina abrasive, was used in sandblasting.

Comparative Example 7

Helioplate HD 6 (manufactured by HelioScience) was used as a skin substitute membrane.

Example 1-6

The surface of one side of ACRYLITE 000 (manufactured by Mitsubishi Rayon Co., Ltd.) was sprayed with FUJIRANDOM WA#16 (manufactured by Fuji Manufacturing Co., Ltd.), which is a fused white alumina abrasive, and was subjected to sandblasting using a sand blaster PNEUMA BLASTER (manufactured by Fuji Manufacturing Co., Ltd.). Thereafter, it was cut to be 50 mm square, thereby manufacturing a skin substitute membrane.

Comparative Example 8

Plexiglas (manufactured by Schoenberg) was used as a skin substitute membrane.

Comparative Example 9

Helioplate (manufactured by HelioScience) was used as a skin substitute membrane.

Table 3 illustrates the characteristics of the skin substitute membranes of Examples 2-1 through 2-8 and 1-4 through 1-6 and Comparative Examples 4 through 9.

TABLE 3

| | ARITHMETIC MEAN ROUGHNESS Sa OF SURFACE OF SKIN SUBSTITUTE MEMBRANE [μm] | ARITHMETIC MEAN ROUGHNESS Sa OF SURFACE OF PLANAR PORTIONS [μm] | WIDTH OF DEPRESSED PORTIONS [μm] | DEPTH OF DEPRESSED PORTIONS [μm] |
|---|---|---|---|---|
| EXAMPLE 2-1 | 20 | 3 | 300 | 80 |
| EXAMPLE 2-2 | 17 | 6 | 250 | 70 |
| EXAMPLE 2-3 | 30 | 1 | 400 | 100 |
| EXAMPLE 2-4 | 13 | 10 | 200 | 60 |
| EXAMPLE 2-5 | 19 | 3 | 300 | 80 |
| EXAMPLE 2-6 | 18 | 3 | 250 | 80 |
| EXAMPLE 2-7 | 25 | 1 | 200 | 80 |
| EXAMPLE 2-8 | 30 | — | 300 | 80 |
| EXAMPLE 1-4 | 16 | — | — | — |
| COMPARATIVE EXAMPLE 4 | 2 | — | — | — |
| COMPARATIVE EXAMPLE 5 | 6 | — | — | — |
| EXAMPLE 1-5 | 16 | — | — | — |
| COMPARATIVE EXAMPLE 6 | 2 | — | — | — |
| COMPARATIVE EXAMPLE 7 | 6 | — | — | — |
| EXAMPLE 1-6 | 16 | — | — | — |
| COMPARATIVE EXAMPLE 8 | 2 | — | — | — |
| COMPARATIVE EXAMPLE 9 | 6 | — | — | — |

The arithmetic mean roughness Sa was measured for the surfaces and the planar portions of the skin substitute membranes using a confocal microscope (manufactured by Lasertech Corporation).

Table 4 illustrates the evaluation results of the skin substitute membranes of Examples 2-1 through 2-8 and 1-4 through 1-6 and Comparative Examples 4 through 9.

TABLE 4

| | DIFFERENCE IN UV RADIATION SPECTRAL TRANSMITTANCE BETWEEN BEFORE AND AFTER GLYCERIN APPLICATION | VARIATION IN SIMPLE ESTIMATED in vitro SPF | CORRELATION BETWEEN ESTIMATED in vitro SPF AND in vivo SPF |
|---|---|---|---|
| EXAMPLE 2-1 | ○ | ⊚ | ⊚ |
| EXAMPLE 2-2 | ○ | ⊚ | ⊚ |
| EXAMPLE 2-3 | ○ | ⊚ | ⊚ |
| EXAMPLE 2-4 | ○ | ⊚ | ⊚ |
| EXAMPLE 2-5 | X | ○ | Δ |
| EXAMPLE 2-6 | X | ○ | Δ |
| EXAMPLE 2-7 | X | ○ | Δ |
| EXAMPLE 2-8 | ○ | ○ | Δ |
| EXAMPLE 1-4 | ○ | Δ | ⊚ |
| COMPARATIVE EXAMPLE 4 | ○ | Δ | X |
| COMPARATIVE EXAMPLE 5 | ○ | Δ | X |
| EXAMPLE 1-5 | X | Δ | ○ |

TABLE 4-continued

| | DIFFERENCE IN UV RADIATION SPECTRAL TRANSMITTANCE BETWEEN BEFORE AND AFTER GLYCERIN APPLICATION | VARIATION IN SIMPLE ESTIMATED in vitro SPF | CORRELATION BETWEEN ESTIMATED in vitro SPF AND in vivo SPF |
|---|---|---|---|
| COMPARATIVE EXAMPLE 6 | X | Δ | X |
| COMPARATIVE EXAMPLE 7 | X | Δ | X |
| EXAMPLE 1-6 | X | X | ⊚ |
| COMPARATIVE EXAMPLE 8 | X | X | X |
| COMPARATIVE EXAMPLE 9 | X | X | X |

The differences in ultraviolet radiation spectral transmittance between before and after application of glycerin show that the skin substitute membranes of Examples 2-1 through 2-4 and 2-8 have high ultraviolet radiation spectral transmittances because their groove-shaped depressed portions are chamfered. The skin substitute membranes of Examples 2-5 through 2-7 have slightly lower ultraviolet radiation spectral transmittances because their planar portions are provided with non-chamfered roughness although their groove-shaped depressed portions are chamfered. On the other hand, it is shown that the skin substitute membranes of Example 1-4 and Comparative Examples 4 and 5 are provided with chamfered roughness to have high ultraviolet radiation spectral transmittances. Further, the variations in simple estimated in vitro SPFs show that the skin substitute membranes of Examples 2-1 through 2-8 have good reproducibility of application of an external preparation for skin because of formation of groove-shaped depressed portions. Further, the correlations between estimated in vitro SPFs and in vivo SPFs show that the skin substitute membranes of Examples 2-1 through 2-4 have large averages of coefficients of correlation $R^2$ because their groove-shaped depressed portions are chamfered and their planar portions are provided with chamfered roughness. On the other hand, it is shown that the skin substitute membranes of Examples 1-4 through 1-6 have large averages of coefficients of correlation $R^2$ because their surfaces are large in arithmetic mean roughness Sa.

A description is given below of the evaluation method of the skin substitute membranes.

[Difference in Ultraviolet Radiation Spectral Transmittance Between Before and after Application of Glycerin]

The transmission spectra of the skin substitute membranes of Examples 2-1 through 2-8 and 1-4 through 1-6 and Comparative Examples 4 through 9 were measured using a spectrophotometer U-4100 (manufactured by Hitachi, Ltd.). Here, the transmission spectra were 290 nm to 400 nm in wavelength with a wavelength step of 1 nm. Further, five samples were measured per skin substitute membrane, and five points, near the center and near the midpoints between the center and the four corners, were measured per sample.

Next, 1.00 mg/cm² of glycerin was applied on the skin substitute membranes of Examples 2-1 through 2-8 and 1-4 through 1-6 and Comparative Examples 4 through 9 by applying and spreading glycerin with a finger with a fingerstall. Thereafter, the same as described above, the spectral transmission spectra were measured using the spectrophotometer U-4100 (manufactured by Hitachi, Ltd.).

Further, the difference in the average of spectral transmittances for light of 300 nm in wavelength between before and after application of glycerin was calculated for each of the skin substitute membranes. This difference was determined as ○ if the difference was less than 5% and x if the difference was more than or equal to 5% relative to the average of spectral transmittances of the skin substitute membrane for light of 300 nm in wavelength before application of glycerin.

[Variation in Simple Estimated In Vitro SPF]

The spectral transmission spectra of the skin substitute membranes of Examples 2-1 through 2-8 and 1-4 through 1-6 and Comparative Examples 4 through 9 were measured using a spectrophotometer U-4100 (manufactured by Hitachi, Ltd.). Here, the spectral transmission spectra were 290 nm to 400 nm in wavelength with a wavelength step of 1 nm. Further, five samples were measured per skin substitute membrane, and five points, near the center and near the midpoints between the center and the four corners, were measured per sample.

Next, ten specialists applied 2.00 mg/cm² of Standard Sample P3 (see Non-Patent Document 3) on the skin substitute membranes of Examples 2-1 through 2-8 and 1-4 through 1-6 and Comparative Examples 4 through 9 by applying and spreading the same with fingers with fingerstalls for one minute, and they were dried at 25° C. for 15 minutes. Thereafter, the transmission spectra were measured using the spectrophotometer U-4100 (manufactured by Hitachi, Ltd.) in the same manner as described above. At this point, each of the specialists applied Standard Sample P3 (see Non-Patent Document 3) on five samples per skin substitute membrane.

Further, the spectrum of a xenon arc ultraviolet radiation light source (see Non-Patent Document 3) was multiplied by the spectral transmittances of each of the skin substitute membranes for light of 290 nm to 400 nm in wavelength before and after application of Standard Sample P3 to be weighted with an erythema index (see CIE 1987) and integrated, thereby determining erythemal effectiveness values.

Next, the ratio of the erythemal effectiveness value of each point of each of the skin substitute membranes before application of Standard Sample P3 to the erythemal effectiveness value of each point of each of the skin substitute membranes after application of Standard Sample P3, that is, a simple estimated in vitro SPF, was calculated.

Further, with respect to each of the skin substitute membranes on a specialist basis, the averages of the simple estimated in vitro SPF of the five points were calculated, and using the averages, the coefficient of variation CV was calculated from the average of the five samples and a standard deviation. The skin substitute membranes were determined as ⊚ if the average of the coefficients of variations CV of the ten specialists was less than 15%, ○ if the average of the coefficients of variations CV of the ten specialists was more than or equal to 15% and less than 20%, Δ if the average of the coefficients of variations CV of the ten specialists was more than or equal to 20% and less than 25%, and x if the average of the coefficients of variations CV of the ten specialists was more than or equal to 25%.

[Correlation Between Estimated In Vitro SPF and In Vivo SPF]

Ten kinds of external preparations for skin having predetermined in vivo SPFs (see FIG. 7) were prepared.

Ten specialists applied 2.00 mg/cm² of the external preparations for skin on the skin substitute membranes of Examples 2-1 through 2-8 and 1-4 through 1-6 and Comparative Examples 4 through 9 by applying and spreading the external preparations for skin with their fingers with fingerstalls for one minute, and they were dried at 25° C. for 15 minutes. At this point, each of the specialists applied each external preparation for skin on five samples per skin substitute membrane.

Next, the estimated in vitro SPFs were measured according to an in vitro SPF evaluation method (see Miura, Y. et al.; "Photochemistry and Photobiology," 2008, 84, 1569-1575) using the ultraviolet radiation transmission characteristic evaluation apparatus 10 illustrated in FIG. 6, and the coefficients of correlation with in vivo SPFs $R^2$ were determined. The skin substitute membranes were determined as ⊚ if the average of the coefficients of correlation $R^2$ of the ten specialists is more than or equal to 0.85, ○ if the average of the coefficients of correlation $R^2$ of the ten specialists is more than or equal to 0.70 and less than 0.85, Δ if the average of the coefficients of correlation $R^2$ of the ten specialists is more than or equal to 0.60 and less than 0.70, and x if the average of the coefficients of correlation $R^2$ of the ten specialists is less than 0.60.

The invention claimed is:

1. A skin substitute membrane, comprising:
    a surface on one side including a plurality of groove-shaped depressed portions and a plurality of planar portions, each of the planar portions being surrounded by the plurality of groove-shaped depressed portions, each of the depressed portions having a cross section having a chamfered V-letter shape, the surface having an arithmetic mean roughness Sa of more than or equal to 10 μm to less than or equal to 50 μm,
    wherein each of the depressed portions has a width of more than or equal to 50 μm to less than or equal to 500 μm and a depth of more than or equal to 30 μm to less than or equal to 150 μm,
    the skin substitute membrane has a thickness of 0.2 mm to 5 mm, and a spectral transmittance for light of more than or equal to 290 nm to less than or equal to 400 nm in wavelength is more than or equal to 50% and less than or equal to 100%, and
    each of the planar portions is provided with chamfered roughness, and has an arithmetic mean roughness Sa of more than or equal to 0.1 μm to less than or equal to 30 μm.

2. The skin substitute membrane as claimed in claim 1, wherein a difference in a spectral transmittance for light of 300 nm in wavelength between before and after application of 1 mg/cm² of glycerin is less than 5%.

3. The skin substitute membrane as claimed in claim 1, comprising:
    polymethylmethacrylate.

4. A skin substitute membrane, comprising:
    a surface provided with chamfered roughness and having an arithmetic mean roughness Sa of more than or equal to 13 μm to less than or equal to 30 μm,
    wherein the skin substitute membrane has a thickness of 0.2 mm to 5 mm, and a spectral transmittance for light of more than or equal to 290 nm to less than or equal to 400 nm in wavelength is more than or equal to 50% and less than or equal to 100%.

5. The skin substitute membrane as claimed in claim 4, wherein a difference in a spectral transmittance for light of 300 nm in wavelength between before and after application of 1 mg/cm² of glycerin is less than 5%.

6. The skin substitute membrane as claimed in claim 4, comprising:
    polymethylmethacrylate.

7. A mold, comprising:
    a surface on one side including a recess, the recess having a plurality of projecting portions and a plurality of planar portions formed at a bottom surface of the recess, each of the planar portions being surrounded by the projecting portions, the bottom surface of the recess having an arithmetic mean roughness Sa of more than or equal to 10 μm to less than or equal to 50 μm, each of the projecting portions having a cross section having a chamfered inverse V-letter shape,
    wherein each of the projecting portions has a width of more than or equal to 50 μm to less than or equal to 500 μm and a height of more than or equal to 30 μM to less than or equal to 150 μm, and
    each of the planar portions is provided with chamfered roughness, and has an arithmetic mean roughness Sa of more than or equal to 0.1 μm to less than or equal to 30 μm.

8. A method of evaluating an external preparation for skin, comprising the steps of
    applying the external preparation for skin on the skin substitute membrane as claimed in claim 1; and
    measuring an ultraviolet radiation transmission characteristic and/or reflection characteristic of the external preparation for skin by exposing the skin substitute membrane having the external preparation for skin applied thereon to light containing ultraviolet radiation.

9. The method of evaluating the external preparation for skin as claimed in claim 8, wherein the ultraviolet radiation transmission characteristic and/or reflection characteristic is measured using at least one selected from the group consisting of an in vitro SPF evaluation method, an in vitro UVA evaluation method, an in vitro PPD method, an in vitro PFA method, an in vitro UVA PF method, a critical wavelength method, a UVA/UVB ratio method, an Australian/New Zealand method, a German DIN UVA balance method, and an SPF/UVA PF (PPD) ratio method.

10. The method of evaluating the external preparation for skin as claimed in claim 8, wherein an amount of application of the external preparation for skin is more than or equal to 1.20 mg/cm² and less than or equal to 2.40 mg/cm².

11. A method of evaluating an external preparation for skin, comprising the steps of:
    applying the external preparation for skin on the skin substitute membrane as claimed in claim 4; and
    measuring an ultraviolet radiation transmission characteristic and/or reflection characteristic of the external preparation for skin by exposing the skin substitute membrane having the external preparation for skin applied thereon to light containing ultraviolet radiation.

12. The method of evaluating the external preparation for skin as claimed in claim 11, wherein the ultraviolet radiation transmission characteristic and/or reflection characteristic is measured using at least one selected from the group consisting of an in vitro SPF evaluation method, an in vitro UVA evaluation method, an in vitro PPD method, an in vitro PFA method, an in vitro UVA PF method, a critical wavelength method, a UVA/UVB ratio method, an Australian/New Zealand method, a German DIN UVA balance method, and an SPF/UVA PF (PPD) ratio method.

13. The method of evaluating the external preparation for skin as claimed in claim 11, wherein an amount of application of the external preparation for skin is more than or equal to 1.20 mg/cm$^2$ and less than or equal to 2.40 mg/cm$^2$.

14. A skin substitute membrane, comprising:
a surface on one side including a groove-shaped depressed portion and a planar portion, the depressed portion having a cross section having a chamfered V-letter shape, the surface having an arithmetic mean roughness Sa of more than or equal to 13 μm to less than or equal to 30 μm, wherein the depressed portion has a width of more than or equal to 200 μm to less than or equal to 400 μm and a depth of more than or equal to 60 μm to less than or equal to 100 μm, the skin substitute membrane has a thickness of 0.2 mm to 5 mm, and a spectral transmittance for light of more than or equal to 290 nm to less than or equal to 400 nm in wavelength is more than or equal to 50% and less than or equal to 100%, and the planar portion is provided with chamfered roughness, and has an arithmetic mean roughness Sa of more than or equal to 1 μm to less than or equal to 10 μm, so that a difference in a spectral transmittance for light of 300 μm in wavelength between before and after application of 1 mg/cm$^2$ of glycerin is less than 5%.

\* \* \* \* \*